United States Patent [19]
Siczek

[11] Patent Number: 5,386,447
[45] Date of Patent: Jan. 31, 1995

[54] MAMMOGRAPHIC SCREENING AND BIOPSY APPARATUS

[75] Inventor: Bernard W. Siczek, Boulder, Colo.

[73] Assignee: Fischer Imaging Corporation, Denver, Colo.

[21] Appl. No.: 949,731

[22] Filed: Sep. 23, 1992

[51] Int. Cl.⁶ ............................................. A61B 6/04
[52] U.S. Cl. ...................................... 378/37; 378/196
[58] Field of Search .......................... 378/37, 195, 196

[56] References Cited

U.S. PATENT DOCUMENTS

| | | | |
|---|---|---|---|
| 2,707,662 | 5/1955 | Goldfield et al. | 311/6 |
| 3,165,630 | 1/1965 | Bielat et al. | 250/58 |
| 3,609,355 | 9/1971 | Schwarzer | 250/50 |
| 3,963,933 | 6/1976 | Henkes, Jr. | 250/456 |
| 3,973,126 | 8/1976 | Redington et al. | 250/444 |
| 4,051,380 | 9/1977 | Lasky | 250/451 |
| 4,099,880 | 7/1978 | Kano | 356/164 |
| 4,485,819 | 12/1984 | Igi | 128/660 |
| 4,545,385 | 10/1985 | Pirschel | 128/660 |
| 4,613,122 | 9/1986 | Manabe | 269/322 |
| 4,618,973 | 10/1986 | Lasky | 378/37 |
| 4,727,565 | 2/1988 | Ericson | 378/205 |
| 4,750,487 | 6/1988 | Zanetti | 128/303 |
| 4,791,934 | 12/1988 | Brunnett | 128/653 |
| 4,869,247 | 8/1989 | Howard, III et al. | 128/303.1 |
| 4,875,478 | 10/1989 | Chen | 128/303 |
| 4,890,311 | 12/1989 | Saffer | 378/99 |
| 4,930,143 | 5/1990 | Lundgren et al. | 378/37 |
| 5,078,142 | 1/1992 | Siczek | 378/37 |

OTHER PUBLICATIONS

Bolmgren et al. "Stereotaxic Instrument for Needle Biopsy of the Mamma", *Am J. Roentgenol*, 129, pp. 121–125 (Jul. 1977).
Dowlatshahi, M. D., "The Needle Replaces the Knife—Exploring Stereotactic Guided Needle Biopsy", *Administrative Radiology*, Jun. 1989, pp. 28–31.
Haight et al., "Radiologists Spread Their Wings: A Look at the Possibilities in Stereotactic Breast Biopsy", *Administrative Radiology*, Nov. 1987, pp. 87–89.
Svane, M. D., "Stereotactic Needle Biopsy", *Administrative Radiology*, Nov. 1987, pp. 90–92.
Azavedo et al., "Stereotactic Fine-Needle Biopsy in 2594 Mammographically Detected Non-Palpable Lesions", reprinted from *The Lancet*, May 13, 1989, pp. 1033–1036.
Evans, M. D., et al., "Needle Localization and Fine-Needle Aspiration Biopsy of Nonpalpable Breast Lesions with Use of Standard and Stereotactic Equipment", *Radiology*, vol. 173, No. 1, Oct., 1989 pp. 53–56.
Dowlatshahi, M. D., et al., "Nonpalpable Breast Tumors: Diagnosis with Sterotaxic Localization and Fine-Needle Aspiration", *Radiology*, vol. 170, No. 2, Feb. 1989, pp. 427–433.

*Primary Examiner*—Craig E. Church
*Attorney, Agent, or Firm*—Sheridan Ross & McIntosh

[57] ABSTRACT

An apparatus (10) for use in performing medical procedures on a breast of a patient is disclosed. The apparatus (10) includes a frame assembly (12) for supporting the patient having an opening (22) therein through which the patient's breasts are permitted to protrude, an imaging system (18) for identifying any suspicious lesions within the patient's breasts, and a biopsy assembly (20) for use in performing a biopsy on the patient's breasts. The frame assembly (12) is tiltable from a vertical position to a non-vertical position to facilitate mammography and the mammographic biopsy procedure. In addition, the imaging system (18) and biopsy assembly (20) are moveable across the patient's chest from one breast to the other. The imaging system (18) is also rotatable and tiltable relative to the patient's breasts to obtain oblique views of the breasts.

13 Claims, 4 Drawing Sheets

MAMMOGRAPHIC SCREENING AND BIOPSY APPARATUS

FIELD OF THE INVENTION

The present invention relates generally to mammography and analysis or treatment of suspicious breast lesions and, more particularly, to an apparatus for use in mammographic screening and diagnosis as well as in medical procedures involving insertion of a medical instrument into a suspicious breast lesion, the apparatus having an improved flexibility of movement so as to simplify and enhance the efficacy of such procedures.

BACKGROUND OF THE INVENTION

A number of medical procedures involve identification of, localization of, and/or insertion of a medical instrument into a suspicious breast lesion. For example, such procedures may be utilized to detect or diagnose the nature of a lesion, to ablate or remove a lesion, to deliver a drug or other treatment to the lesion, or to mark a pathway to the lesion for use in subsequent open surgery.

One application of such procedures relates to the detection of breast cancer. Breast cancer is a leading cause of death of women in the United States. Early detection and analysis of breast lesions suspected of being cancerous is therefore of great importance. Accordingly, women increasingly undergo routine mammography to detect suspicious lesions which may not be palpable and which can therefore escape detection through self-examination. In many cases, an initial screening or diagnostic mammography procedure identifies a suspicious lesion which can then be analyzed through a biopsy procedure.

Detection of non-palpable lesions can be accomplished through x-ray imaging. In order to obtain a complete image of a breast, two x-ray images per breast, e.g., a top or cranial-caudal view and a side or medial-lateral view, are commonly utilized although some believe that a single, oblique view, commonly called a "Cleopatra" view, may be sufficient for this purpose. As used herein, the phrase "oblique views" refers to views of a breast from directions transverse to the plane in which conventional top and side views are taken. Current mammographic systems generally do not provide positioning flexibility to easily obtain a Cleopatra view. Thus, a complete imaging procedure normally involves obtaining four x-ray views, two views per breast. This can be time consuming and exposes the patient to four intervals of x-ray radiation. Similarly, due to the lack of flexibility in positioning current mammographic systems to the patient's breasts, the patient is ordinarily positioned to the equipment, e.g., the patient is ordinarily moved in order to sequentially examine the left and right breasts, and the patient's breast and arms are moved with the assistance of an operator in order to achieve a high quality mammographic image, thereby further complicating the procedure.

If a suspicious lesion is identified through screening or diagnostic mammography, further definition of the nature of the lesion, i.e., malignant or benign, normally involves surgical biopsy of the suspicious area following a needle localization procedure to mark the non-palpable lesion for the surgeon. Needle biopsy procedures of either fine needle aspiration (i.e., to obtain cell samples for cytological analysis) or core biopsy (i.e., to obtain a tissue sample for histological analysis) are gaining acceptance as a minimally invasive alternative to surgical excisional biopsy. In this regard, it will be appreciated that tissue samples from core biopsy are preferred over cell samples because such samples permit histological examination of the lesion, not merely cytological examination, thereby providing a definitive diagnosis and reducing or eliminating the need for a specialized cytologist.

The screening and diagnostic mammography and certain stereotaxic needle biopsy procedures have generally been performed with the patient either in a vertical sitting or standing position or in a face down, horizontal position, wherein one of the patient's breasts protrudes through an opening in the examination table. The sitting or standing position is advantageous for certain procedures as easy access to the breast is provided for the technologist and equipment. In addition, the sitting or standing procedures do not require an examination table mounting and dismounting process which can be difficult for some patients. On the other hand, the horizontal position has been found advantageous in that the breast is pendulantly disposed thereby facilitating positioning of the breast for mammographic procedures and access to lesions near the chest wall. In addition, the horizontal position allows small breasts to be compressed more efficiently. Such breast compression is desired during mammographic procedures. The horizontal position also enhances patient comfort and reduces the likelihood of movement of the breast during a mammographic and particularly a needle biopsy procedure. Further, a safety advantage is obtained when the patient is in a horizontal position as there is always a risk of fainting during the procedure.

SUMMARY OF THE INVENTION

Accordingly, objects of the present invention include the following.

The provision of an apparatus for use in mammographic procedures which permits improved efficacy of screening and diagnostic mammography as well as medical procedures involving insertion of a medical instrument into the patient's breast.

The provision of an apparatus for use in mammographic procedures wherein the patient can be reclined enough from a vertical position so that her breasts project pendulantly, and wherein the patient can be inclined from a horizontal position for convenient breast access.

The provision of an apparatus for use in mammographic procedures wherein the patient is supported on a frame which is tiltable so that the patient can be inclined at angles selected to facilitate particular screening and diagnostic mammography as well as needle biopsy procedures.

The provision of an apparatus for use in mammographic procedures which is positionable relative to the patient's breasts and, more specifically, moveable across the patient's chest from one breast to the other.

The provision of an apparatus for use in mammographic procedures wherein the apparatus provides an additional degree of freedom in positioning relative to the patient so as to enhance single view screening of a breast, to allow more breast tissue to be viewed on one mammographic image, and to provide increased flexibility of biopsy instrument positioning.

The provision of an improved apparatus for use in mammographic needle biopsy procedures wherein a tissue sample suitable for histological examination or a cell sample can be reliably obtained through a minimally invasive needle biopsy technique.

Additional objectives and corresponding advantages of the present invention will be apparent to those skilled in the art upon consideration of the present specification.

The present invention discloses a mammographic apparatus suitable for use in both screening and diagnostic mammography, as well as in medical procedures such as needle biopsy which involve insertion of a medical instrument to a point of interest within the patient's breast, which apparatus enhances the efficacy of such procedures. The apparatus has an improved flexibility of movement which permits improved imaging for a single view of a breast and sequential examination of both of a patient's breasts substantially without moving the patient. In addition, the invention also allows for realization of the advantages associated with vertical and horizontal patient positioning. The apparatus also enhances accurate and reliable placement of a biopsy needle so that tissue or cell samples suitable for histological or cytological examination can be obtained without surgery.

According to one aspect of the present invention, an apparatus is provided which comprises a tiltable frame for supporting the patient including an opening to allow passage of at least one of the patient's breasts therethrough, an instrument mounted on the frame means for use in performing medical procedures on the patient's breast, and a mechanism for selectively moving the frame and instrument across a range of orientations relative to vertical so as to allow the patient and frame to be positioned at orientations selected to facilitate performance of medical procedures using the instrument. In this regard, it will be appreciated that positions reclined even slightly from vertical will allow the patient's breast to be projected outward due to gravity so that advantages associated with conventional horizontal positioning can be obtained. Similarly, positions inclined even slightly from horizontal provide improved access to the patient's breast such that advantages associated with conventional vertical positioning can be obtained. The positioning of the patient for particular procedures can be selected based on considerations of patient comfort and safety, the size of the patient, the location of a lesion, ease of access for the physician and equipment and other factors. Accordingly, the frame may be moveable across a range of positions from a substantially vertical position to a substantially horizontal position. The frame can be moveable to positions past vertical or horizontal if desired. The movement of the frame can be accomplished manually or may be automated, e.g., directed by a computer controlled motor.

According to another aspect of the present invention, an imaging system is provided which improves breast imaging and allows oblique views of a breast to be obtained. The imaging system, which can be interconnected to a frame for supporting the patient in a sitting or standing position, comprises a transmitter for transmitting an imaging beam, such as a radiographic or other radiation beam, through the patient's breast and a receiver for receiving at least a portion of the beam transmitted through the patient's breast. The transmitter can include a conventional x-ray source or a laser and the receiver can include an x-ray film tray or a charge-coupled imaging device or the like for substantially instantaneous electronic imaging. At least one of the transmitter and receiver can be rotatable about an axis extending forwardly from the patient's breast to permit various views of the breast to be obtained. Additionally, at least one of the transmitter and receiver can be rotatable about an axis substantially parallel to the patient's cranial-caudal axis to obtain oblique views. Alternatively, the frame can be moveable in a cradle motion to obtain oblique views. It will thus be appreciated that an imaging system constructed in accordance with the present invention provides a flexibility of movement sufficient to obtain a wide variety of views including Cleopatra views.

According to a further aspect of the present invention, an apparatus for use in performing medical procedures on a patient's breasts is provided which reduces or eliminates the need to reposition the patient during such procedures. The apparatus comprises a frame for supporting the patient and an imaging system for imaging a breast. A mechanism for providing relative movement between the frame and the imaging system is provided such that the imaging system is moveable across the patient's chest from one breast to the other. This can be accomplished by moving the frame and/or the imaging system. The frame is provided with at least one opening to allow passage of the patient's breasts therethrough. In this regard, a single opening dimensioned to allow passage of both breasts or separate openings for each breast may be provided.

According to a still further aspect of the present invention, an apparatus for performing medical procedures on a breast includes a frame for supporting a patient and a puncture instrument for use in performing a breast biopsy. The puncture instrument may include a biopsy needle for obtaining cell or tissue samples from the patient's breast. For example, the puncture instrument may comprise a spring-loaded biopsy gun. The puncture instrument and frame can be movably interconnected such that the puncture instrument is moveable across the patient's chest from one breast to the other. In addition, the puncture instrument can be rotatable about a first axis extending forwardly from the patient's breast and about a second axis substantially parallel to the patient's cranial-caudal axis.

BRIEF DESCRIPTION OF THE DRAWINGS

For a more complete understanding of the present invention and for further advantages thereof, reference is now made to the following detailed description taken in conjunction with the drawings in which.

DETAILED DESCRIPTION OF THE PREFERRED EMBODIMENT

Figure 1:
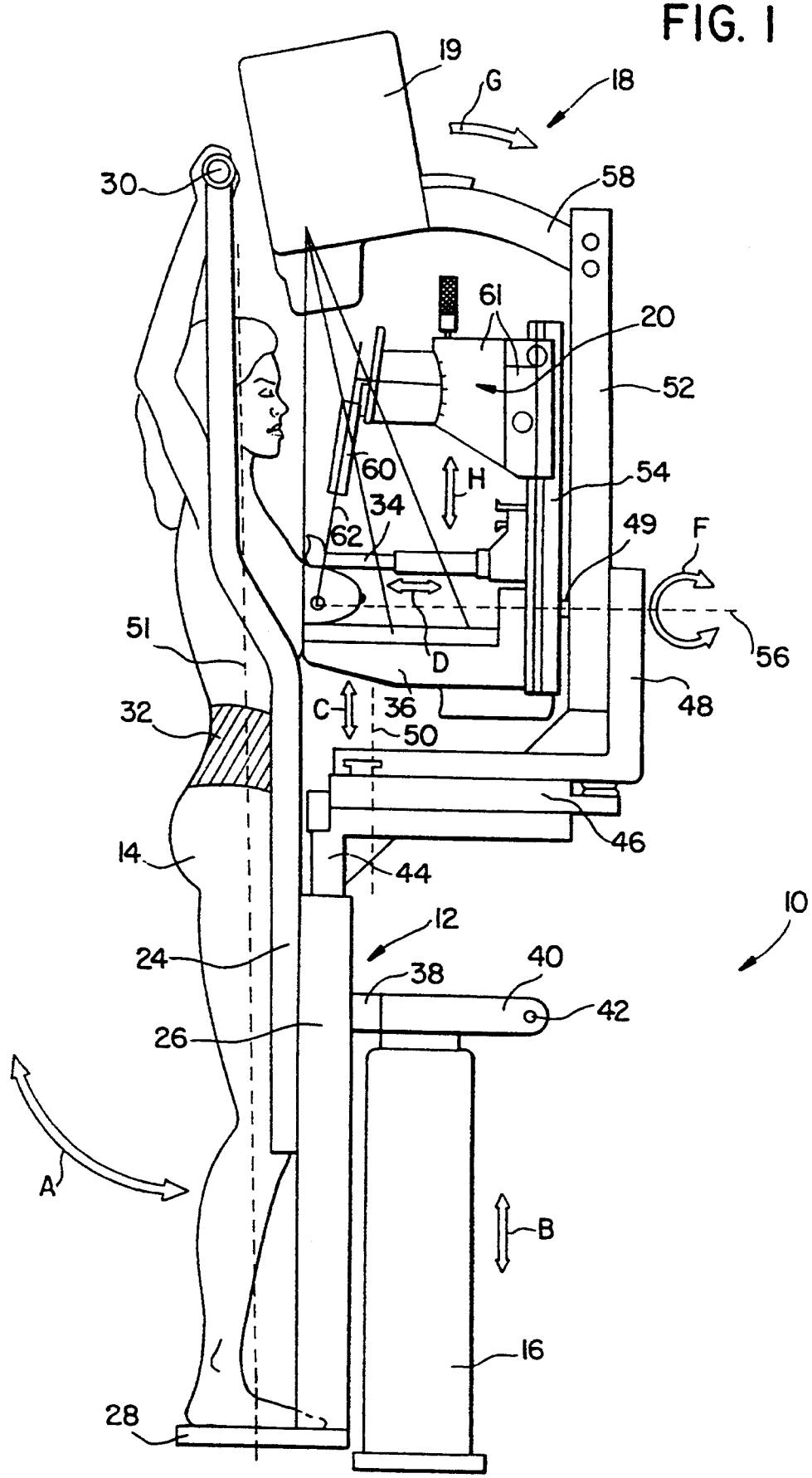
FIG. 1 is a side view of an apparatus constructed in accordance with the present invention in a substantially vertical position.

Referring to FIGS. 1-4, an apparatus constructed in accordance with the present invention is generally identified by the reference numeral 10. Generally, the apparatus 10 comprises a frame assembly 12 for supporting a patient 14 in a prone position pivotally mounted on a pedestal 16 or other support member, a mammography imaging system 18 comprising an imaging beam source 19 and receiver including film tray 36 for imaging the patient's breasts so as to identify any suspicious lesion therein, and a detachable needle biopsy assembly 20 for extracting a cell or tissue sample from any identified lesion.

The frame assembly 12 supports the patient 14 in a prone position wherein the patient's breasts are permitted to protrude through an opening 22 in the frame assembly 12. Although in the illustrated embodiment both of the patient's breasts protrude through a single opening 22, it will be appreciated that separate openings for each breast could be provided or a moveable window, door or diaphragm could be provided to permit exposure of only a single breast or portion thereof. The frame assembly 12 comprises an elongated patient support member 24 interconnected to the top end of a central structural member 26 and a platform 28 interconnected to the bottom end of and extending rearwardly away from the central structural member 26. A handle 30 is provided across the top of patient support member 24 for gripping and an optional restraining belt 32 is centrally disposed across the patient support member 24 for enhanced patient stabilization.

The patient 14 can stand on platform 28 and grip handle 30 as shown such that the patient's breast received between compression paddle 34 and film tray 36 during a medical procedure such as a mammographic biopsy procedure. Alternatively, a second paddle juxtaposed between the breast and film tray 36 in opposed relation to first paddle 34 could be utilized to stabilize the breast if direct contact between the breast and film tray 36 is not desired. In place of or in addition to the illustrated grip handle 30, individual handles (not shown) may be provided underneath the frame assembly 12 so that the patient can grip such handles with her pectoral muscles relaxed. The patient 14 is thus supported by the support member 24 in combination with the platform 28 and handle 30. As will be explained in greater detail below, the patient 14 is further supported by compression paddle 34 which also serves to hold the patient's breast stationary during the course of the mammographic biopsy procedure. Further support may be provided, for example, by way of a fabric strip attached to the frame assembly 12 and extending across the patient's upper body if desired.

The frame assembly 12 is mounted on pedestal 38, which in turn is mounted on the floor, in a manner which allows the frame assembly 12 to be tilted (as shown by arrow A) and raised or lowered (arrow B). It will be appreciated that the frame assembly 12 could alternatively be supported by an arm extending from a wall or ceiling or other support member. In this manner, the patient 14 can be supported by the frame assembly 12 at a tilt angle suitable for the procedure being performed as described above. For example, a biopsy procedure may be performed with the frame assembly 12 inclined slightly relative to horizontal such that the patient's breast protrudes pendulantly through the opening 22 and is readily accessible to the physician. Access to the patient's breast can be further enhanced by raising frame assembly 12.

In the illustrated embodiment, the frame assembly 12 can be raised or lowered by operation of a first actuator (not shown) housed in pedestal 16. The actuator, which is interconnected to frame assembly 12 by arm 38 and 40, can comprise, for example, a pneumatic or hydraulic cylinder or a linear screw actuator. In this manner, the frame assembly 12 and patient 14 can be raised as shown by arrow B to provide easier access to the patient's breast for the physician. A vertical adjustment range of about ten inches at a rate of about one inch per second has been found to be adequate for this purpose.

Figure 2:
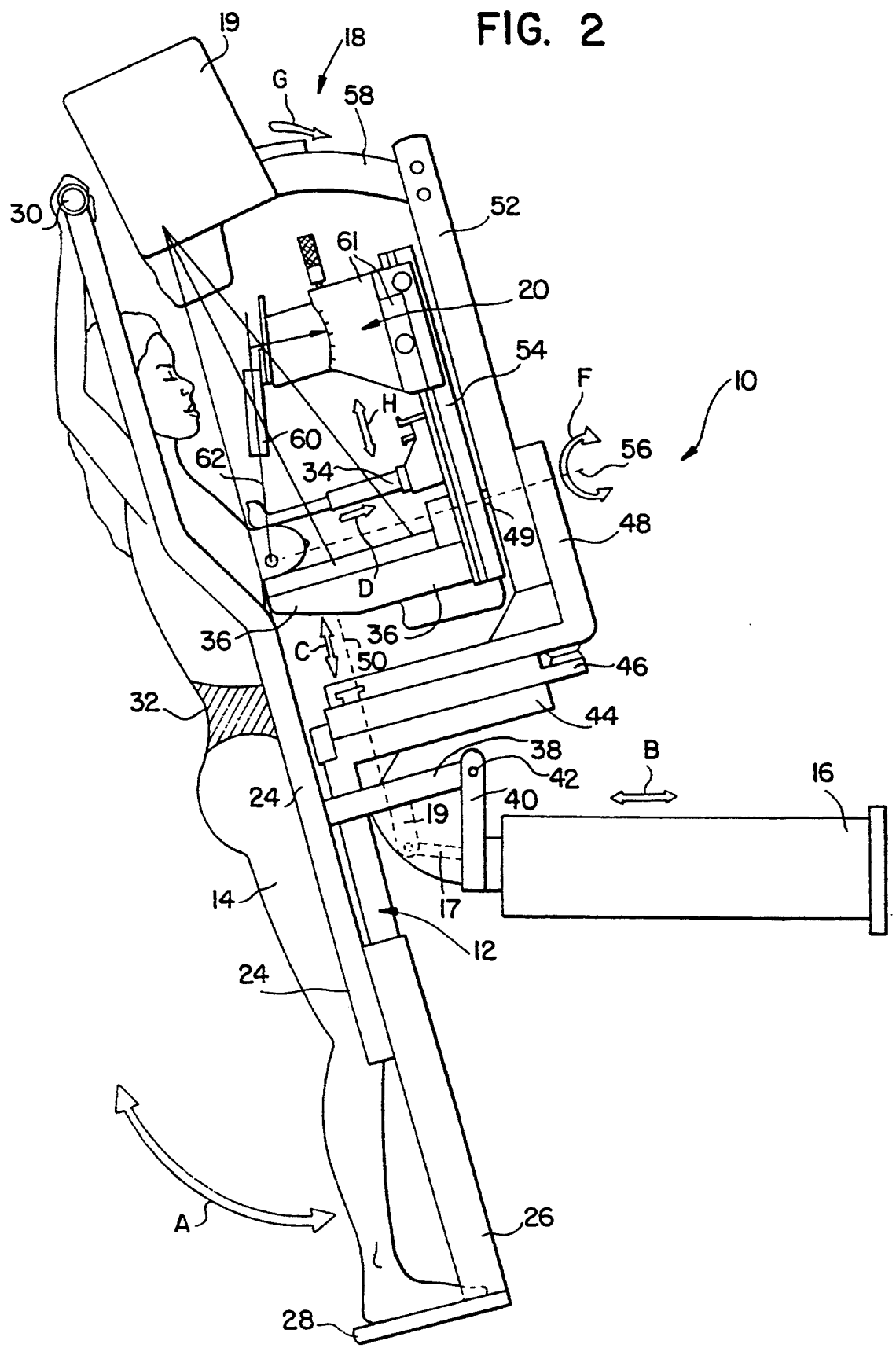
FIG. 2 is a side view of the apparatus of FIG. 1 in a non-vertical position.

Access to the patient's breast can be further enhanced by tilting the frame assembly 12. In this regard, it will be appreciated that improved access to the breast, as compared with horizontal patient positioning, is provided by tilting the patient 14 slightly from horizontal as shown in FIG. 2. In the illustrated embodiment, arms 38 and 40 are pivotably interconnected at pin 42 such that the frame assembly 12 can be pivoted by extension or retraction of actuator 17 which is interconnected to lever arm 19 (FIG. 2). The frame assembly 12 and patient 14 can thus be tilted by pivoting arm 38 relative to arm 40. It should be noted that the patient 14 is simultaneously raised and tilted by this pivotal motion. This pivotal motion is preferably controlled by a computer driven motor which can be programmed to accurately repeat selected positions. The illustrated frame assembly 12 is tiltable across an approximately 90° range, from a substantially vertical position to a substantially horizontal position, at a rate of about 4.5° per second. It will be appreciated that this tilting motion, in addition to providing flexibility in adjusting patient positioning for improved access and physician convenience, allows the patient 14 to mount and dismount the apparatus 10 in a standing position, thereby eliminating side mounting and dismounting procedures associated with known mammographic tables which procedures are difficult for some patients.

The frame assembly 12 is interconnected to imaging system 18 and biopsy assembly 20 by a generally "L" shaped support member 44. The support member 44 is engaged with member 26 in a telescopic sliding arrangement such that the imaging system 18, biopsy assembly 20, compression paddle 34 and associated components can be longitudinally moved relative to the frame assembly 12 to allow adjustment for patients of various heights. That is, the frame assembly 12 can be raised or lowered so that the patient's breast is properly positioned on the film tray 36. As will be described below, the film tray 36 can also be raised and lowered (as shown by arrow C) as needed. A sliding adjustment range of about eight inches is believed to be sufficient to accommodate most patients. This adjustment is preferably motorized such that the physician can easily make fine adjustments during the course of medical procedures.

A carriage arm 46 is slidably mounted on support member 44 such that the imaging system 18, biopsy assembly 20, compression paddle 34 and associated components can be moved forwardly and rearwardly, i.e., towards and away from the patient 14 (arrow D). In this manner, the film tray 36 and compression paddle 34 can be properly positioned to the patient's breast. In the illustrated embodiment, the carriage arm movement is motorized to move across an eight inch range at a rate of about 0.4 inches per second. Although this range is greater than patient anatomy requires, such movement permits changing of the tray during medical procedures.

A generally "L" shaped support member 48 is mounted on the carriage arm 46 in a manner which permits the following movements of member 48 with respect to arm 46. First, the member 48 is slidably mounted on arm 46 such that the member 48 and components supported thereon can be moved across the patient's chest (arrow E of FIG. 3). It will be appreciated that medical procedures can therefore be performed sequentially on the patient's left and right breasts substantially without moving the patient 14. In addition, the member 48 is pivotably mounted on arm 46 such that the member 48 and components mounted thereon can be rotated about axis 50 (arrow F). It will be appreciated upon consideration of the description below that this latter movement allows the imaging system 18 including film tray 36 to be positioned such that an oblique, Cleopatra view of the breast can be obtained. A single Cleopatra view is believed by some to be sufficient for screening, thereby reducing or eliminating the need for conventional top and side views of the breast. Additionally, this motion allows the biopsy gun to approach the breast from oblique angles. It is believed that a rotational motion of about 15° is sufficient for this purpose, although a greater range rotational motion may be provided if desired. This rotational motion can be motorized so that tilting at a rate of about 2° per second can be achieved.

Transmitter arm 52 and receiver arm 54 are pivotably mounted on support member 48 via pin 49 such that the arms 52 and 54 can be rotated, in unison or separately, about axis 56 as shown by arrow F. Preferably, axis 56 is arranged to be substantially coincident with an axis extending forwardly from a point of interest within the patient's breast so that the components mounted thereon can be rotated about the breast, i.e., moved circumferentially relative to the base of the breast. In this regard, it will be appreciated that it is desirable to rotate the imaging system 18 and biopsy assembly 20 relative to the patient's breast to facilitate particular mammographic biopsy procedures. In this illustrated embodiment, the receiver arm is manually rotatable around the patient's breast across a 105° range. The transmitter arm 54 is rotatable across a 120° range, such movement being motorized at a rate of about 10° per second.

Imaging beam source 19 is slidably carried by arcuate arm 58 mounted on transmitter arm 52. The source 19 can thus be manually moved along arcuate arm 58 as shown by arrow G over a range of approximately 15° to provide a desired beam angle, for example, based on the location of a lesion with respect to the patient's chest wall, and to avoid the heads of patients who are unable to straighten their backs. The beam source 19 provides a beam which can be transmitted through the patient's breast for imaging thereof. In this regard, X-ray, laser imaging or other suitable imaging equipment may be utilized. The illustrated beam source 19 comprises a conventional x-ray beam source.

The receiver arm 54 carries film tray 36, compression paddle 34, and detachable biopsy assembly 20. It will be appreciated that any suitable receiver for receiving a portion of the beam transmitted through the patient's breast and providing an image of the breast may be utilized. For example, the receiver may comprise an x-ray imaging film holder, a charge-coupled device or similar device for obtaining real time or quasi-real time imaging. The illustrated apparatus 10 includes a conventional x-ray film tray 36.

The patient's breast is held in compression between the film tray 36 and compression paddle 34 to reduce breast movement and enhance the accuracy of mammographic biopsy procedures. The compression paddle 34 is slidably mounted on receiver arm 54 as shown by arrow H so that the paddle 34 can be moved to compressingly engage or release the patient's breast. The paddle 34 is also extendable and retractable, towards and away from the patient 14, to facilitate engagement of the patient's breast. The motion of the paddle 34, like all motions of equipment to engage the patient's breast, should be manual or slowly motorized for safety. In addition, where such motions are motorized, a manual release should be provided to release the breast in case of emergency.

Biopsy assembly 20 is detachably connected to receiver arm 54 so that the assembly can be removed during routine mammography as may be desired. Any suitable breast biopsy instrument, including various manual or driven biopsy needle insertion instruments, can be utilized in accordance with the present invention. The illustrated assembly 20 can be constructed and interconnected to the receiver arm 54 as described in U.S. Pat. No. 5,078,142, incorporated herein by reference. Generally, the illustrated assembly 20 comprises a spring loaded biopsy gun 60 for driving biopsy needle 62 into a preselected point within the patient's breast, typically, a suspicious lesion. The spring loaded biopsy gun 60 can comprise, for example, the BIOPTY gun marketed by the Bard Urological Division of C. R. Bard, Inc., Covington, Ga. The gun 60 is mounted on receiver arm 54 by way of moveable support members 61 controlled by micrometers such that the gun can be aimed at the point of interest. The support members may be angularly and/or linearly moveable to aim the gun 60. In addition, a depth stopper controls the insertion depth of the needle 62. The micrometers and depth stopper can be set manually or position encoders and a motorized positioner for automatically setting the proper linear position or angle and depth parameter values may be utilized. The needle 62 can be a narrow gauge needle suitable for fine needle aspiration of cells or a wider gauge needle for obtaining tissue samples suitable for histological examination. In this regard, good results have been obtained with a 14 gauge biopsy needle. However, care should be exercised in particular cases in selecting a needle to provide an adequate sample for diagnosis while minimizing the likelihood of complications.

Conveniently, the movements of various portions of the apparatus 10 described above can be motorized and remotely controlled through a foot or hand operated controller in a manner known in the art. In particular, it may be desired to remotely control the patient height and tilt angle adjustments, the angles of the arms 52 and 54, the positioning of the compression paddle 34, and the targeting of the gun 60. In this manner, the physician can quickly position the apparatus 10 and patient 14 with minimal disruption to ongoing medical procedures. In addition, the various movements can be controlled by a computer or the like in a manner which permits positions to be accurately repeated as may be desired.

A mammographic biopsy procedure can be performed in accordance with the present invention as follows. Initially, the patient 14 can mount the apparatus 10 in a vertical position by standing on platform 28 and gripping handle 30. Belt 32 may be used to secure the patient 14 to the apparatus 10 and reduce patient movement. Thereafter, the frame assembly 12 and patient 14 can be tilted to a suitable angle for screening. The film tray 36 can then be vertically positioned to the patient's breast and rotated and tilted relative to the breast so as to obtain a position suitable for a Cleopatra imaging view. Alternatively, conventional top and side imaging views or the like may be utilized. The beam source 19 can then be positioned so that a beam can be projected through the breast and impinge on film to provide an image of the breast which can be analyzed to identify suspicious lesions.

If a suspicious lesion is identified, the location of the lesion can be ascertained through stereotaxic imaging. The frame assembly 12 and patient 14 can then be tilted to an angle suitable for performing a biopsy procedure. Similarly, the imaging system 18 and biopsy assembly 20 can be rotated relative to the breast to an angle selected to facilitate needle biopsy, including an angle that would allow the breast to be approached posteriorly. The beam source 19 can then be moved to obtain two views of the breast which can be used to obtain the spatial coordinates of the lesion by a known stereotaxic method, such as that described in U.S. Pat. No. 5,078,142. Finally, the spatial coordinates can be used to position the spring loaded gun 60 and the gun 60 can be operated to obtain a sample from the lesion for diagnosis.

Figure 3:
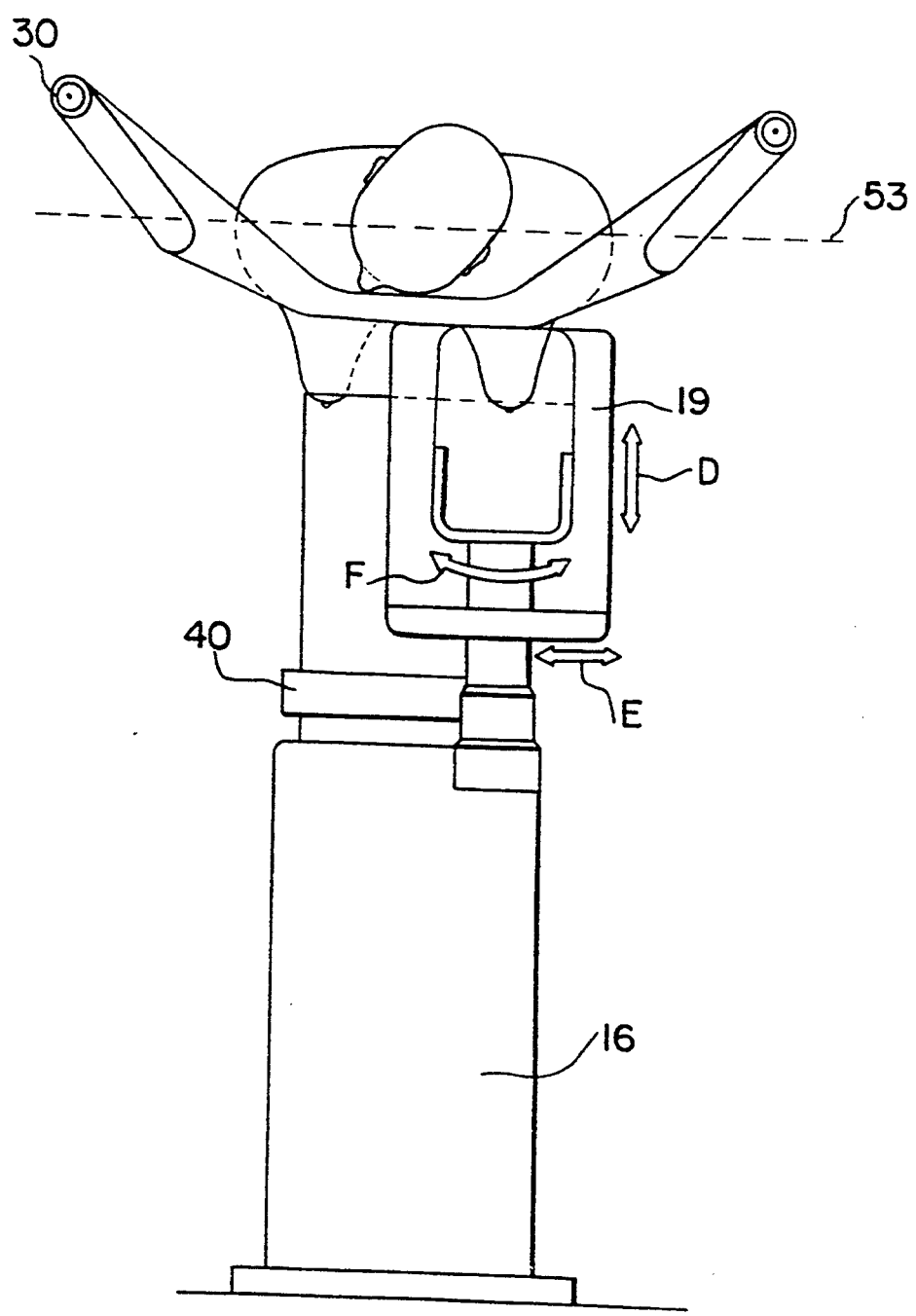
FIG. 3 is a top view of the apparatus of FIG. 1.
Figure 4:
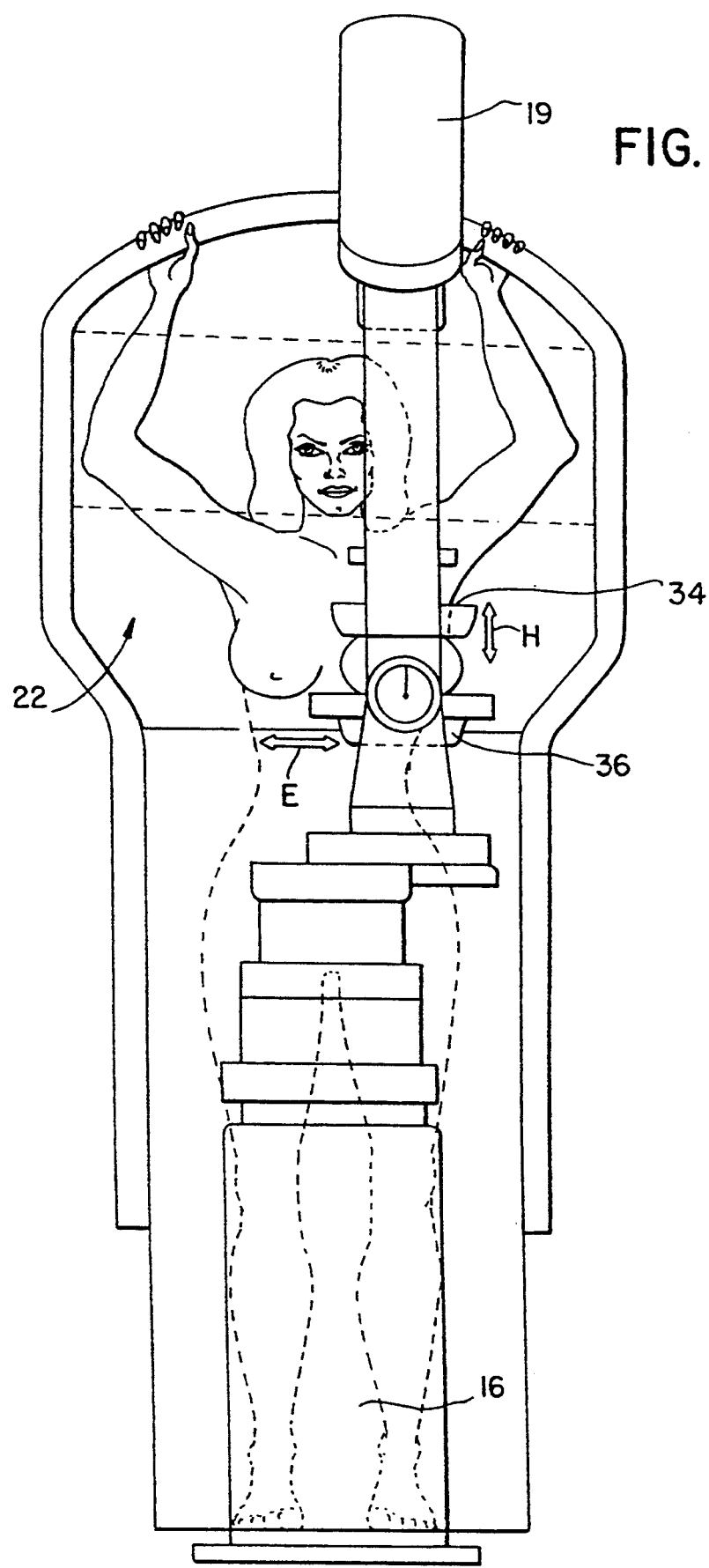
FIG. 4 is a front view of the apparatus of FIG. 1 in a substantially horizontal position.

It will be appreciated that the increased freedom of movement of the apparatus 10 enhances both mammographic imaging and biopsy. In this regard, each of the beam source 19, film tray 36 and biopsy assembly 20 is rotatable about axis 56 extending forwardly from the patient's breast and about axis 50 which is generally parallel to the cranial-caudal axis 51 (FIG. 1). Thus, a variety of viewing angles and biopsy gun approach positions and angles can be obtained thereby enhancing access to and imaging of the patient's breasts. For example, the apparatus can obtain viewing angles and biopsy gun approach angles transverse to the plane containing the patient's cranial-caudal axis 51 and medial-lateral axis 53 (FIG. 3).

In addition, once a lesion is localized, various procedures can be conducted through a cannula to treat or eliminate the lesion. For example, cryoablation, laser ablation, hyperthermia, or other techniques can be used to kill cancer cells in situ as directed by the stereotaxic device. Similarly, certain minimally invasive surgical techniques such as percutaneous removal of the lesion can be directed by the stereotaxic device.

While various embodiments of the present invention have been described in detail, it is apparent that further modifications and adaptations of the invention will occur to those skilled in the art. However, it is to be expressly understood that such modifications and adaptations are within the spirit and scope of the present invention.

What is claimed is:

1. An apparatus for use in performing medical procedures on breasts of a patient comprising;
    frame means for supporting said patient including at Least one opening through which said patient's breasts are permitted to protrude;
    imaging means for providing a radiographic image of said patient's breasts, the imaging means including transmitting means for transmitting a beam through said patient's breasts and receiving means for receiving at least a portion of said transmitted beam passing through said patient's breasts; and
    first movement means for providing relative movement between said frame means and said imaging means so as to move between a first relative position for imaging a first breast of said patient and a second relative position for imaging a second breast of said patient.

2. The apparatus of claim 1, wherein said first movement means is operatively connected to said imaging means to move said imaging means across said patient's chest.

3. The apparatus of claim 1, wherein said imaging means is rotatably mounted relative to said frame means for rotation about a first axis extending forwardly from one of said patient's breasts and for rotation about a second axis substantially parallel to the cranial-caudal axis of said patient.

4. The apparatus of claim 1, further comprising tilting means for moving said frame means between a first position wherein said patient is supported in a substantially vertical orientation and a second position wherein said patient is tilted relative to vertical so that said patient's breast protrudes pendulantly through said opening.

5. The apparatus of claim 1, further comprising puncture instrument means mounted on said frame means for inserting a needle into said patient's breast.

6. An apparatus for use in performing medical procedures on a breast of a patient, comprising:
    means for supporting said patient;
    imaging means for providing an image of said patient's breast, the imaging means including transmitting means for transmitting a beam through said patient's breast and receiving means for receiving at least a portion of said transmitted beam passing through said patient's breast; and
    means for rotating at least one of said transmitting means and said receiving means about an axis substantially parallel to the cranial-caudal axis of said patient so as to obtain an oblique view of said breast.

7. An apparatus for use in performing medical procedures on a breast of a patient, comprising:
    frame means for supporting said patient including an opening to allow passage of at least one of said patient's breasts therethrough;
    tilting means for moving said frame means between a first position wherein said patient is supported in a substantially vertical orientation and a second position wherein said patient is tilted relative to vertical so that patient's breast protrudes pendulantly through said opening;
    imaging means for providing an image of said patient's breast, the imaging means including transmitting means for transmitting a beam through said patient's breast and receiving means for receiving at least a portion of said transmitted beam passing through said patient's breast;
    positioning means for rotating said imaging means about said patient's breast and tilting said imaging means so as to obtain an oblique view of said breast; and
    puncture instrument means mounted on said frame means for inserting a needle into said patient's breast.

8. An apparatus for use in performing medical procedures on a breast of a patient, comprising:
    frame means for supporting said patient including an opening to allow passage of at least one of said patient's breasts therethrough;
    imaging means for obtaining an image of said patient's breast including transmitting means for transmitting a signal through said patient's breast and receiving means for receiving at least a portion of said transmitted signal passing through said patient's breast; and tilting means for selectively moving said frame means and imaging means across a range of orientations relative to horizontal so as to allow the patient and frame means to be positioned at orientations selected to facilitate performance of said medical procedures on said patient's breast using said imaging means.

9. The apparatus of claim 8, wherein said transmitting means is movably mounted to said frame means for movement forwardly and rearwardly relative to said patient.

10. The apparatus of claim 8, wherein at least one of said transmitting means and said receiving means is rotatably mounted to said frame means for rotation about an axis substantially parallel to the cranial-caudal axis of said patient.

11. The apparatus of claim 8, wherein at least one of said transmitting means and said receiving means is rotatably mounted to said frame means for rotation about an axis extending forwardly from said patient's breast.

12. The apparatus of claim 8, wherein at least one of said transmitting means and said receiving means is rotatably mounted to said frame means for rotation about an axis substantially parallel to the medial-lateral axis of said patent.

13. The apparatus of claim 8, wherein said imaging means is movably mounted to said frame means for relative movement across said patient's chest.

* * * * *